Figure 1:
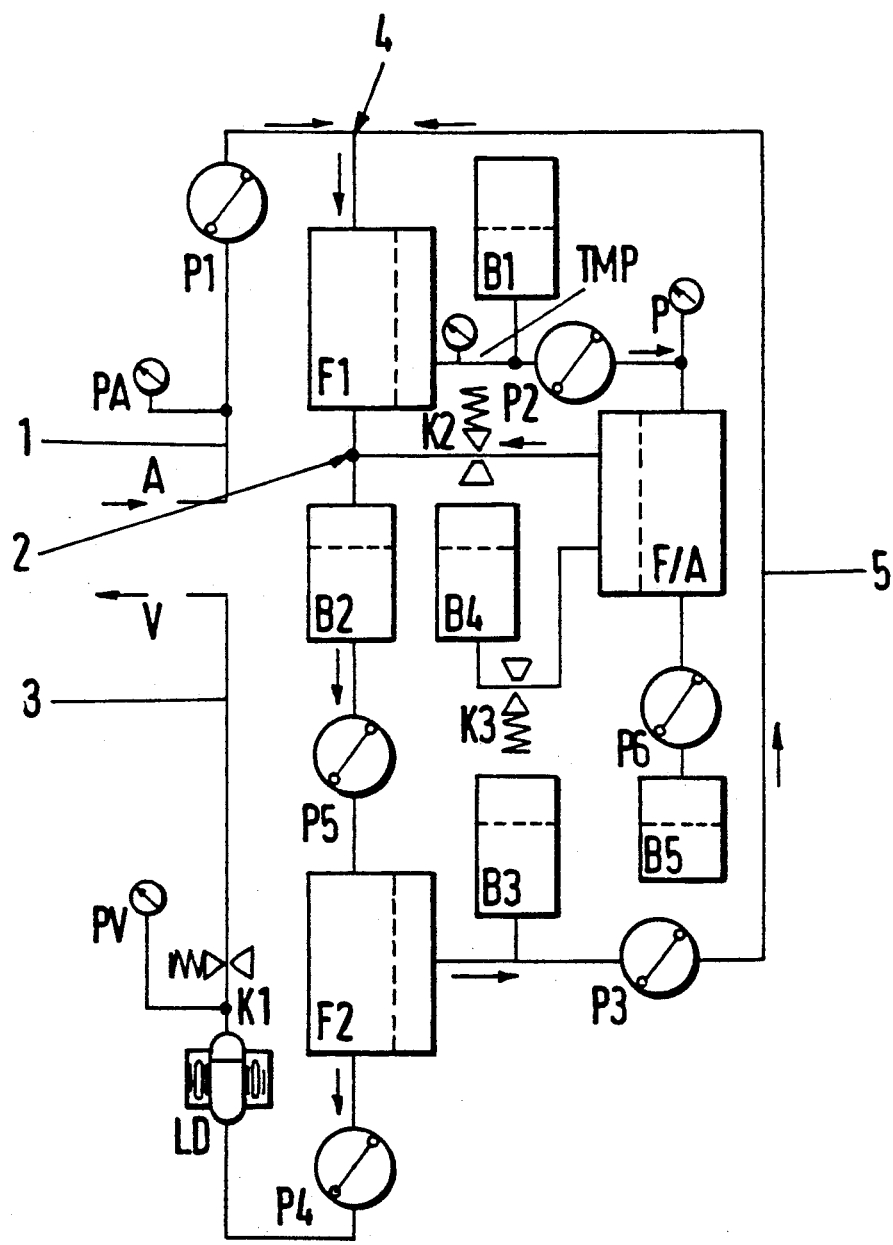

United States Patent [19]
Flaig et al.

[11] Patent Number: 5,108,612
[45] Date of Patent: Apr. 28, 1992

[54] METHOD AND A DEVICE FOR THE SELECTIVE ELIMINATION OF PLASMA COMPONENTS FROM BLOOD

[75] Inventors: Hans-Jürgen Flaig, Lauterbach; Hans v. Baeyer, Berlin, both of Fed. Rep. of Germany

[73] Assignee: Fresenius AG, Fed. Rep. of Germany

[21] Appl. No.: 565,504

[22] Filed: Aug. 10, 1990

[30] Foreign Application Priority Data

Aug. 22, 1989 [DE] Fed. Rep. of Germany ....... 3927633

[51] Int. Cl.[5] .............. B01D 61/14; B01D 61/18; B01D 61/22
[52] U.S. Cl. ...................... 210/651; 210/90; 210/137; 210/195.1; 210/195.2; 210/202; 210/295; 210/691; 210/767; 210/805; 210/806; 210/321.6; 604/6
[58] Field of Search ............... 210/650, 651, 660, 691, 210/692, 767, 782, 789, 787, 805, 806, 90, 137, 143, 194, 195.1, 195.2, 202, 295, 321.6, 321.65; 604/4, 5, 6; 530/412, 415, 427

[56] References Cited

U.S. PATENT DOCUMENTS

| | | | |
|---|---|---|---|
| 4,185,629 | 1/1980 | Cullis et al. | 604/6 |
| 4,834,888 | 5/1989 | Polaschegg | 210/806 |
| 4,851,126 | 7/1989 | Schoendorfer | 210/782 |
| 4,871,462 | 10/1989 | Fischel et al. | 210/321.87 |
| 4,923,439 | 5/1990 | Seidel et al. | 604/6 |
| 5,057,226 | 10/1991 | Antwiler | 210/806 |

FOREIGN PATENT DOCUMENTS 232885 8/1987 European Pat. Off. .
3245591 6/1984 Fed. Rep. of Germany .

Primary Examiner—W. Gary Jones
Attorney, Agent, or Firm—Andrus, Sceales, Starke & Sawall

[57] ABSTRACT

A method and a device for the selective elimination of plasma components from blood, by means of which the blood is diluted with a diluting material prior to separation of the plasma therefrom. The blood diluted in this manner is separated from its plasma components in a separation filter and the plasma components are exclusively processed and the recombined with the corpuscular blood components and freed of the diluting solution.

21 Claims, 1 Drawing Sheet

METHOD AND A DEVICE FOR THE SELECTIVE ELIMINATION OF PLASMA COMPONENTS FROM BLOOD

The invention relates to a method and a device for the selective elimination of plasma components from blood, in which the method is performed to separate plasma from the blood by means of a separation filter and then, before the plasma is remixed with the corpuscular blood components, a segregating device is used to remove the respective plasma components. As regards the apparatus aspect, the invention relates to an arrangment comprising a blood feed device, a separation filter for the separation of the plasma from the blood, a segregating device for removal of the respective plasma components, a mixing device for mixing the processed plasma with the corpuscular components of the blood and a blood returning device.

In hemaphersis, blood components are eliminated in an extracorporal circulation system. The equipment used for this purpose typically comprises a separation filter or a plasma separator, with the aid of which the corpuscular blood components are segregated. While the corpuscular components are passed through the equipment substantially without any processing, it is possible to pass the blood plasma through further filtering or segregating devices in order to remove certain blood components therefrom.

The selective and specific elimination of plasma components may be described in a particularly effective manner with reference to LDL apheris,. In LDL apheris, low density lipoprotein (LDL) is removed from the plasma. LDL apheris is performed for instance in the case of patients with genetically caused hyperlipoproteinemia of the IIa type. Various methods have been proposed for this, as for instance membrane differential filtration, immuno adsorption or heparin precipitation. In all these methods in a first respective stage the plasma is separated from the corpuscular blood components so that the blood plasma may then be separately processed or treated. In the known methods the separation of the plasma from the blood is performed by means of a plasma filter or a centrifuge, and in the second circuit, which forms the plasma circuit, it is possible to use membrane differential filters or immuno adsorbers.

In the known methods and equipment it has turned out to be a disadvantage that in the processing of the plasma the degree of elimination is limited both as regards the apparatus and as regards the method technique. On the one hand it is a disadvantage that in the case of membrane filters the receiving capacity is limited by the blocking of the pores and in the case of adsorbers there are similar problems. Although it is possible to reactivate the filtering effect of the membrane module or membrane filter by reverse flow through the membrane, this procedure makes the apparatus more complex and leads to a general increase in costs and in the time taken for treating a patient. The same applies for desorption, by means of which the adsorbing capacity of the adsorber column may be restored by using a two column procedure The method limitation with respect to the elimination capacity is due to the fact that, for instance in the case of LDL elimination, the volumne of blood plasma obtained in the first method step is decisive for the further treatment in the second treatment stage. In a way dependent on the plasma volume, limiting values will naturally occur which apply for the elimination of the plasma components.

The German patent publication 3,245,591 A describes a method involving the dilution of the plasma to be treated prior to feed thereof into an LDL segregating device. In this case as well there has been found to be the drawback that the plasma volume separated from the patient's blood cannot itself be increased so that here as well the maximum amount of plasma components to be eliminated is restricted.

One object of the present invention is to devise a method and equipment of the type mentioned which are simple, are reliable in use and make possible a selective elimination of plasma components while at the same time maintaining a high efficiency.

As regards the method, the invention provides the feature that the blood is diluted prior to separation of the plasma by means of a diluting solution and after mixing of the processed plasma with the corpuscular blood components the said solution is removed from the blood again.

The method in accordance with the invention is characterized by a series of substantial advantages. Since in accordance with the invention the blood itself is diluted prior to separation of the blood plasma from the blood, it becomes possible to greatly increase the blood plasma yield. Because in the following part of the method the elimination of the plasma components depends on the overall plasma volume present, the invention leads to a substantial enhancement of the process efficiency.

In an advantageous further development of the method in accordance with the invention there is a feature in accordance with which the blood is diluted with a ratio of at least 1 part blood to 2 parts diluting solution. Thus there is an amount of blood as required for separation of the plasma at the separation filter, such amount being at least twice as large as the amount of blood taken from the patient. The overall yield of plasma is thus able to be substantially increased.

In accordance with a particularly suitable form of the method in accordance with the invention, the diluting solution is returned after the concentration of the blood and fed back into the circuit. As regards the treatment of the blood plasma there is a circulation system for the diluting solution, such circuit leading to certain advantages, more particularly economic ones. As an alternative it is however also possible to use the diluting solution only once and to take it up in a suitable collecting container.

The diluting solution preferably used is a phosphate-buffered physiological sodium chloride solution.

As regards the apparatus the object of the invention is to be attained by providing a diluting device upstream from the separation filter in order to dilute the feed blood with a diluting solution and downstream from the mixing device there is a removal device in order to segregate the diluting solution from the blood. Thus the invention ensures that even prior to entry into the separation filter the patient's blood is diluted to a sufficient extent and it is at the same time possible to avoid any of the diluting solution being returned to the patient. The dilution solution thus only functions to keep the blood in a diluted state when flowing along a part of the path it has to follow.

The apparatus in accordance with the invention is best so designed that the removing device for separation of the diluting solution from the diluted blood comprises a hemofilter.

In order to make possible recirculation of the removed dilution solution, the removal device is connected with the diluting device by means of a return line.

Furthermore it is possible to have a storage means, used for the dilution solution, adjacent to the return line. This storage means may for instance be in the form of a bag and serve to allow for changes in volume in the system, as for instance at the commencement of treatment.

In accordance with the invention, the segregating device, by which the plasma components to be removed are segregated from the blood plasma, may have the form of an adsorber or a cascade filter. In this respect it is possible to provide for reverse flow through the adsorber or the cascade filter in order to cleanse the membranes thereof.

In accordance with a further possible development of the invention, the device preferably comprises a battery of pumps, that is to say a return pump on the return line, a segregating pump on the feed line running to the segregating device, a fractionating pump between the mixing device and the removal device, an arterial blood pump in the blood feed line and a venous blood pump on the blood return line. By varying the displacement of the arterial blood pump it is possible to control the degree of dilution of the feed blood. Moreover, it is preferred for the sum of the displacements of the arterial blood pump and of the return pump to be equal to the displacement of the fractionating pump so that a constant volumetric rate is fed to and removed from the system.

In order to increase the rate of filtration it has furthermore proved to be an advantage if a device for creating a pulsating flow on the blood side be arranged upstream or downstream from the plasma separator or separation filter or on the filter side upstream from the fractionating module or, respectively, the segregating device.

Further features and advantages of the invention will be gathered from the ensuing detailed description of one possible form thereof referring to the drawing whose single figure diagrammatically shows one possible working embodiment.

The device in accordance with the invention serves for the selective and specific elimination of plasma components from blood and in what follows will be described with reference to a device with which it is possible to perform LDL reduction.

The device in accordance with the invention is connected with the venous blood circulation of the patient by one of number a of possible ways. It is possible to design the connection by using a conventional 2 arm technique, but in an alternative connection a single needle technique is also possible, which then comprises a controller in a conventional manner.

The blood side of the device in accordance with the invention comprises a blood supply device 1 and a blood return device 3, which are in the form of a suitable connection such as a hollow needle or cannula or of a hose.

The blood feed device 1 comprises an arterial pressure sensor PA and an arterial blood pump P1. The blood is fed to a diluting device 4, which in the illustrated working embodiment is in the form of a T tube fitting. However, it is also possible to design the diluting device 4 in the form of a multiway valve, as for example an adjustable flow control valve of this type.

In the diluting device 4 the blood is diluted with a diluting solution, as for instance a sodium chloride solution.

The diluted blood is fed to a separating filter F1 (or plasma separator). The corpuscular blood leaves the separation filter 1 on its way to a mixing device 2, while the plasma is supplied via a segregating pump P2 to a segregating device F/A. On the feed line for the blood plasma there is additionally a TMP pressure sensor and a fractionating pressure sensor P. Furthermore, a plasma bag B1 is arranged on the line in order to serve as a storage means.

In the segregating device F/A the plasma components, which are to be eliminated, are segregated from the plasma.

The plasma emerging from the segregating device F/A is fed under pressure through a return swilling hose clamp K2 to the mixing device 2, in which the blood plasma is mixed with the corpuscular components of the blood. This blood is passed through a bag B2, which thus holds both the corpuscular components and also the processed plasma.

Following the bag B2 there is a fractionating pump P5, by means of which the diluted blood is passed into a removing device F2. In this removing device F2 there is a segregation or removal of the diluting solution, which is fed via a return line to the diluting device 4. The pump P3 is provided on the return line on which a diluting solution bag B3 is also provided.

The blood which is now no longer diluted and which leaves the removal device F2, is fed via a pump P4 (a pump for venous blood) to the blood return device 3. This blood return device 3 furthermore comprises, a venous blood clamp K1, a venous blood pressure sensor PV and an air detector LD.

The separation filter F1 may for instance be a plasma filter as supplied by Fresnius, Federal Republic of Germany, under the trade name of Plasmaflux P2 and which is designed as a membrane filter having a sieve coefficient of nearly unity even when employed for the elimination of substances with a large molecular weight such as for instance immuno complexes of 4—4 Dalton. The removing device F2 (or hemofilter) may for instance be in the form of an Asahi Hemofilter PAN 200. Such filter may for instance have a capillary lumen of $200\mu$ and a capillary wall thickness of 55 $\mu$m. The segregating device FA may either be in the form of a high volume adsorber or of a plasma cascade filter. In the case of the adsorber it is for instance possible to have two adsorbers placed in series (of the type commercially available as Asahi-Cascade Kaneka Liposorbers). The plasma cascade filter may be for instance a Asahi-Cascade AC 1760 filter.

The device in accordance with the invention thus offers the possibility of extracting an amount of LDL in the second treatment stage equal to the amount present in the volume of plasma separated in the first stage. All in all it is thus possible to substantially increase the efficiency of the apparatus.

In the case of the use of a cascade filter as a segregating device F/A there is, during the course of the treatment, at least one reverse flushing operation with isotonic sodium chloride solution. For such reverse flushing the clamp K2 is shut and the pump P2 is stopped so that the flow path in this respect is interrupted. Furthermore the clamp K3 is opened to make possible communication with a bag B4, in which isotonic sodium chloride solution is held. This solution is pumped by the pump P6 through the filter and, respectively, the segregating device and received in the bag B5.

The control of the second stage, in which the blood plasma is treated, takes place with the aid of the pressure as measured by the pressure sensor P upstream from the segregating device F/A. It is an advantage in this respect to provide for computerized control of the flushing cycle in the case of the use of a cascade filter.

The degree of dilution of the blood is set by means of the arterial blood pump P1 and of the return or dilution pump P3. The flow rates of the venous blood pump P4 and of the arterial blood pump P1 are equal in normal operation in order to be able to supply the patient with the removed volumes. In order to concentrate the blood the flow rate of the venous blood pump P4 is smaller than that of the arterial blood pump P1. The sum of the displacements of the arterial blood pump P1 and of the dilution pump P3 is equal the displacement of the fractionating pump P5.

The manner of operation of the arrangement in accordance with the invention will now be described. After connection of a catheter with the patient's blood circulation system the pump P1 is used to supply the blood, which is fed by the blood feed device 1, to the diluting device 4. At the very commencement of the operating cycle the diluting device 4 is supplied with diluting liquid from the storage means B3 by operation of the pump P3. There is thus a dilution of the feed blood, which is supplied in the suitably diluted form to the separation filter F1. In the separation filter F1 the blood plasma is separated and is supplied by means of the pump P2 to the segregating device F/A. Passing through a hose line, which is not shown in detail, and the clamp K2, the blood plasma leaves the plasma circuit and is mixed in the mixing device 2 with the corpuscular blood. The latter passes through a buffer storage device B2 and by means of the pump P5 it is fed to the removing device F2. In the latter there is a segregation of the diluting liquid, which is fed via the pump P3 to the return line 5. The storage means B3 serves both as a storage means for allowing for variations in the amount of liquid during operation and also, as noted above, during the starting up phase. In addition the storage means B3 is used when the blood treating procedure is to be terminated, the return pump P3 preventing a return flow of the diluting liquid. The blood, which after passage through the removal device F2 has been restored to its original concentration, is supplied via the venous blood pump P4 to the body of the patient. In order to forestall any undesired return on termination of the treatment procedure and/or during flushing of the segregating device F/A, the blood return line 3 is additionally fitted with a clamp K1.

In a lab setup with 0.5 liter of entire blood and an adsorber as the fractionating module F/A the following settings were used for the displacements of the individual pumps:

| Arterial blood pump P1 | 30 ml/min. |
| venous blood pump P4 | 30 ml/min. |
| plasma pump P2 | 100 ml/min. |
| dilution pump P3 | 160 ml/min. |
| fractionating pump P5 | 190 ml/min. |

The volumes of the bags were as follows

| Plasma bag B1 | less than 500 ml. |
| fractionated plasma and blood in bag B2 | less than 500 ml. |
| dilution solution in bag B3 | less than 2000 ml. |

The amount of extracorporal blood amounted to approximately 300 ml.

The dilution on the blood side with subsequent concentration involves the following advantages: there is an increase in the plasma yield of the primary plasma separator. Furthermore there is an increase in the effectiveness of the secondary module, in which no channeling occurs. Another point is that an adsorber or a filter may be used selectively as the secondary module in the same device. The segregation is performed in a manner free of substitute. Moreover there is no desorption of the adsorber with toxic solution.

The invention is not limited to the working embodiment described and to one skilled in the art it will be clear that there are further possibilities of modification and development.

We claim:

1. A method for the selective elimination of a plasma component from blood, the blood having a corpuscular portion and plasma portion, said method comprising the steps of:
   providing a stream of blood;
   adding a diluting solution to the blood to form a diluted stream of blood;
   separating the plasma portion and diluting solution from corpuscular portion of the blood;
   removing the selected plasma component from the diluted plasma portion of the blood;
   combining the plasma portion remaining after separation, the diluting solution, and the corpuscular portion to reform the diluted stream of blood; and
   removing the diluting solution from the diluted stream of blood to reform the stream of blood.

2. The method as claimed in claim 1 further defined as adding a diluting solution to the blood in a ratio of at least 1 part blood to 2 parts diluting solution.

3. A method as claimed in claim 1 further defined as adding, to the stream of blood, diluting solution which has been removed from previously treated blood.

4. The method as claimed in claim 1 further defined as adding a diluting solution to the blood comprising a sodium chloride solution.

5. An apparatus for the selective elimination of a plasma component from blood, the blood having a corpuscular portion and a plasma portion, said apparatus comprising:
   a blood feed device for obtaining blood from a source;
   means in fluid communication with said blood feed device for adding a diluting solution to the blood;
   separating means in fluid communication with said adding means for separating the plasma portion and the diluting solution from the corpuscular portion of the blood;
   means for removing the selected plasma component from the diluted plasma portion of the blood, said plasma component removing means being in fluid communication with said separating means;
   means in fluid communication with said separating means and said plasma component removing means for combining the plasma portion remaining after separation, the diluting solution, and the corpuscular portion to reform the diluted blood;

means in fluid communication with said combining means for removing the diluting solution from the blood to reform the blood; and blood discharge means in fluid communication with said diluting solution removing means for discharging blood from said apparatus.

6. The apparatus as claimed in claim 5 wherein said diluting solution removing means comprises a hemofilter.

7. The apparatus according to claim 5 wherein said diluting solution removing means is coupled to said means for adding diluting solution by means of a diluting solution return line, whereby diluting solution removed from the blood can be added to subsequently processed blood.

8. The apparatus as claimed in claim 7 further including a diluting solution storage means coupled to said diluting solution return line.

9. The apparatus as claimed in claim 8 further including pump means in said diluting fluid return line.

10. The apparatus according to claim 7 further including pump means in said diluting fluid return line.

11. The apparatus according to claim 10 wherein said apparatus includes pump means in said blood feed device and wherein said apparatus includes means for controlling the volumetric rate of said blood feed device pump means and said removed diluting solution return line pump means, thereby to control the amount of dilution of the blood.

12. The apparatus according to claim 5 wherein said means for removing the selected plasma component comprises an adsorber.

13. The apparatus according to claim 5 wherein said means for removing the selected plasma component comprises a plasma cascade filter.

14. The apparatus according to claim 5 wherein said means for removing the selected plasma component is further defined as adapted for the passage of a reverse flushing fluid therethrough and wherein said apparatus further includes means for providing said reverse flushing fluid.

15. The apparatus according to claim 5 further including pump means interposed between said separating means and said means for removing the selected plasma component.

16. The apparatus according to claim 5 further defined as including pump means interposed in a fluid communication path extending between said combining means and said means for removing the diluting solution.

17. The apparatus according to claim 16 wherein said apparatus further includes pump means in said blood feed means; wherein said diluting solution removing means is coupled to said means for adding diluting solution by means of a diluting solution return line having pump means; and wherein said apparatus further includes means for controlling the volumetric rate of said pump means such that the sum of the displacements of said blood feed device pump means and of said removed diluting solution return line pump means is equal to the volumetric rate of said pump means interposed in said fluid communication path between said combining means and said diluting solution removing means.

18. The apparatus according to claim 5 wherein said blood feed means includes pump means and wherein said blood discharge means includes pump means.

19. The apparatus according to claim 15 further including a pressure sensor placed upstream from said means for removing the selected plasma component.

20. The apparatus according to claim 15 further including means in fluid communication with said separating means for producing pulsating fluid flow.

21. The apparatus according to claim 20 further defined as including means in fluid communication with said means for removing the selected plasma component for producing pulsating fluid flow.

* * * * *

UNITED STATES PATENT AND TRADEMARK OFFICE
CERTIFICATE OF CORRECTION

PATENT NO. : 5,108,612
DATED : April 28, 1992
INVENTOR(S) : HANS-JURGEN FLAIG ET AL It is certified that error appears in the above-identified patent and that said Letters Patent is hereby corrected as shown below:

CLAIM 19, Col. 8, Line 30, delete "15" and substitute therefore --- 5 ---; CLAIM 20, Col. 8, Line 33, delete "15" and substitute therefore --- 5 ---.

Signed and Sealed this

Twenty-eighth Day of September, 1993

*Attest:*

BRUCE LEHMAN

*Attesting Officer*  *Commissioner of Patents and Trademarks*